United States Patent [19]

Ávár et al.

[11] 4,036,812
[45] July 19, 1977

[54] METHOD OF STABILIZING ORGANIC MATERIALS EMPLOYING PYRAZOLE NICKEL COMPLEXES

[75] Inventors: Lajos Ávár, Binningen; Kurt Hofer, Munchenstein, both of Switzerland

[73] Assignee: Sandoz Ltd., Basel, Switzerland

[21] Appl. No.: 641,678

[22] Filed: Dec. 17, 1975

Related U.S. Application Data

[62] Division of Ser. No. 575,157, May 7, 1975, Pat. No. 3,959,265.

[30] Foreign Application Priority Data

May 13, 1974  Switzerland .................. 6492/74

[51] Int. Cl.$^2$ .............................................. C08K 5/34
[52] U.S. Cl. ............................ 260/45.75 N; 106/176
[58] Field of Search ................. 260/45.75 N; 106/176

[56] References Cited
U.S. PATENT DOCUMENTS 3,939,163  2/1976  Ramey et al. ............... 260/45.75 N

*Primary Examiner*—V.P. Hoke
*Attorney, Agent, or Firm*—Gerald D. Sharkin; Richard E. Vila; Joseph J. Borovian

[57] ABSTRACT

The present invention concerns novel nickel complexes (I) possessing U.V. stabilizing properties characterized by bearing per molecule 2 monodentate nickel coordinated 1,3-hydrocarbyl-4-(greater than $C_1$)-acyl-pyrazole-5-oxy ligands and one bidentate or two monodentate nickel coordinated primary or secondary amine ligands, and their use as U.V. stabilizers for e.g. plastics materials.

8 Claims, No Drawings

METHOD OF STABILIZING ORGANIC MATERIALS EMPLOYING PYRAZOLE NICKEL COMPLEXES

This is a division of application Ser. No. 575,157 filed May 7, 1975, now issued as U.S. Pat. No. 3,959,265.

The present invention relates to nickel complexes useful in the stabilization of sensitive material against the degradative effect of ultraviolet (U.V.) light.

Accordingly, the present invention provides nickel complexes (I) possessing U.V. stabilizing properties characterized by bearing per molecule 2 monodentate nickel coordinated 1,3-hydrocarbyl-4-(greater than $C_1$)acyl-pyrazole-5-oxy ligands and one bidentate or two monodentate nickel coordinated primary or secondary amine ligands.

It is to be understood that by the term "(greater than $C_1$)acyl" is meant a keto radical of the formula

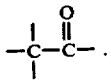

It is also to be understood that the secondary amine ligand may be in the form of a nitrogen-containing heterocycle, e.g. a 5 or 6 membered nitrogen containing heterocycle which may additionally contain a further hetero atom such as oxygen, e.g. piperidino, morpholino, pyrrolidino or imidazolidino.

As will be appreciated, whether the amine can serve as a mono- or bidentate ligand will depend on the nature of the amine. For example, hydroxyalkylamines can serve as bidentate ligands.

As will also be appreciated, the 4-acyl-pyrazole-(5)-oxy moiety may bear substituents on the 1,3-hydrocarbyl substituents attached to the pyrazole ring which do not adversely affect the U.V. stabilizing properties or stability of the complexes. The selection of such substituents forms part of the general knowledge in the U.V. stabilizer art.

A preferred group of complexes of the invention are the complexes of formula Ia,

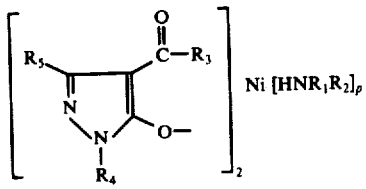

Ia wherein either $R_1$ is hydrogen, alkyl ($C_1$-$C_8$, preferably $C_1$ or $C_2$) or —$CH_2CH_2OH$
and $R_2$ is alkyl($C_1$-$C_{18}$); alkyl($C_1$-$C_{18}$) substituted by 1 hydroxyl, 1 alkoxy($C_1$-$C_4$), 1 piperidino or 1 morpholino substituent; cyclohexyl; phenylalkyl($C_7$ or $C_8$); phenylalkyl($C_7$ or $C_8$) substituted on the phenyl nucleus by 1 or 2 alkyl($C_1$-$C_4$) and/or 1 hydroxyl substituent; phenyl; phenyl substituted by 1 alkyl($C_1$-$C_{12}$), 1 chlorine, 1 phenyl or 1 phenyl substituted by 1 hydroxyl and/or 1 or 2 alkyl($C_1$-$C_4$) substituents;

or $R_1$ and $R_2$ together with the —NH— group to which they are bound form a piperidine, morpholine, pyrrolidine or imidazolidine ring, $R_3$ is alkyl($C_1$-$C_{22}$); alkyl($C_1$-$C_{21}$)-thio-alkyl($C_1$-$C_{21}$) with $C_2$-$C_{22}$ in the aggregate thereof; alkyl($C_1$-$C_4$) substituted by 1 or 2 chlorines; cycloalkyl($C_5$-$C_{12}$); cycloalkyl($C_5$-$C_{11}$)alkyl($C_1$-$C_7$) with $C_6$-$C_{12}$ in the aggregate thereof; phenylalkyl($C_7$-$C_{12}$); phenylalkyl($C_7$-$C_{12}$) substituted on the phenyl nucleus thereof by 1 or 2 hydroxyl and/or 1 or 2 alkyl($C_1$-$C_{12}$), 1 cycloalkyl($C_5$-$C_{12}$) or 1 cycloalkyl($C_5$-$C_{11}$)-alkyl($C_1$-$C_7$) with $C_6$-$C_{12}$ in the aggregate thereof; phenyl; phenyl substituted by 1 or 2 halogen, 1 cyano, 1 meta- or para-hydroxyl, 1 or 2 alkyl($C_1$-$C_{12}$), 1 or 2 alkoxy($C_1$-$C_{12}$), 1 phenyl and/or 1 $R_6$—O— or $R_6$—$SO_2$— substituent wherein $R_6$ is phenyl or phenyl substituted by 1 or 2 alkyl($C_1$-$C_8$) substituents having 1 to 3 substituents and a maximum of $C_{18}$ in the aggregate of the substituents; or a heterocyclic substituent selected from furanyl, thiophenyl, benzothiophenyl, indolyl, pyridyl and quinoxalinyl unsubstituted or substituted by 1 or 2 halogen, 1 or 2 alkyl($C_1$-$C_4$) and/or 1 or 2 alkoxy($C_1$-$C_4$) substituents with a maximum of 2 substituents;

$R_4$ and $R_5$ are each, independently, alkyl($C_1$-$C_8$), phenyl or phenyl substituted by 1 halogen and/or 1 or 2 alkyl($C_1$-$C_4$) substituents, and $p$ is 1 when the amine ligand is bidentate
and $p$ is 2 when the amine ligand is monodentate, i.e. when one or both of $R_1$ and $R_2$ are hydroxyalkyl.

Further preferred are the complexes of formula Ib

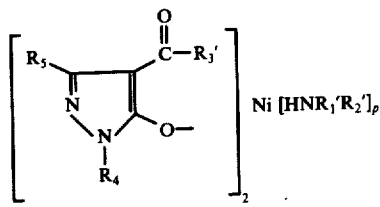

Ib wherein either $R_1'$ is hydrogen or $C_1$ or $C_2$ alkyl,
and $R_2'$ is one of the monovalent significances of $R_2$ and preferably is alkyl($C_1$-$C_8$), 2-hydroxyethyl, cyclohexyl, benzyl, phenyl or phenyl substituted by 1 alkyl($C_1$-$C_{12}$), or $R_1'$ and $R_2'$ together with the —NH— group to which they are bound, form a piperidine, morpholine, pyrrolidine or imidazolidine ring, preferably a piperidine or morpholine ring, $R_3'$ is alkyl($C_1$-$C_{18}$); cycloalkyl($C_6$-$C_8$); phenylalkyl($C_7$-$C_{10}$); phenylalkyl($C_7$-$C_{10}$) substituted on the phenyl nucleus by 1 hydroxyl and/or 1 or 2 alkyl($C_1$-$C_6$) substituents; phenyl; phenyl substituted by 1 or 2 halogen, 1 m- or p-hydroxyl, 1 or 2 alkyl($C_1$-$C_8$), 1 or 2 alkoxy($C_1$-$C_8$) and/or 1 phenyl substituent, with 1 to 3 substituents and a maximum of $C_{12}$ in the aggregate of the substituents; furanyl, thiophenyl or benzothiophenyl; or furanyl, thiophenyl or benzothiophenyl substituted by 1 or 2 halogen or 1 alkyl($C_1$-$C_4$) substituent; and preferably has one of the significances of $R_3''$ as defined below, and $R_4$, $R_5$ and $p$ are as defined above.

Still further preferred are the complexes of formula Ic,

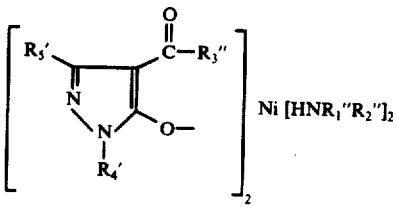

wherein either $R_1''$ is hydrogen and
$R_2''$ is alkyl($C_1$–$C_{18}$), cyclohexyl, benzyl, phenyl or phenyl substituted by 1 alkyl($C_1$–$C_{12}$),
or $R_1''$ and $R_2''$, together with the —NH— group to which they are bound, form a morpholine ring,
$R_3''$ is alkyl($C_3$–$C_{18}$); cyclohexyl; phenylethyl; phenylethyl substituted on the phenyl nucleus by 1 hydroxyl and/or 1 or 2 alkyl($C_1$–$C_4$) substituents; phenyl; phenyl substituted by 1 chlorine, 1 m- or p-hydroxyl, 1 or 2 alkyl($C_1$–$C_4$), 1 alkoxy($C_1$–$C_4$) and/or 1 phenyl substituent, with 1 to 3 substituents and a maximum of $C_{12}$ in the aggregate of the substituents; furanyl, thiophenyl or benzothiophenyl; or furanyl, thiophenyl or benzothiophenyl substituted by 1 chlorine or 1 $C_1$ or $C_2$ alkyl substituent;
$R_4'$ is methyl, phenyl or phenyl substituted by 1 alkyl($C_1$–$C_4$),
and $R_5'$ is alkyl($C_1$–$C_4$) or phenyl.

Of particular interest are the complexes of formula Id,

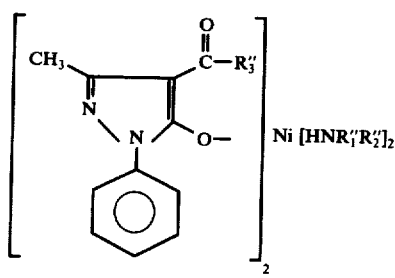

wherein $R_1''$, $R_2''$ and $R_3''$ are as defined above.

By the term "halogen" as employed herein is meant chlorine or bromine, preferably chlorine.

By the term "alkyl" as employed herein where this contains more than two carbon atoms is meant straight or branched chain primary, secondary, or where appropriate, tertiary alkyl.

When $R_1$ and $R_2$ together with the —NH— group to which they are bound form a heterocyclic ring, this is preferably a piperidine or morpholine ring and more preferably a morpholine ring.

When $R_2$ is alkyl, this is preferably unsubstituted.

When $R_2$ is substituted alkyl, this is preferably hydroxy substituted alkyl($C_2$–$C_4$) and is especially 2-hydroxyethyl.

When $R_2$ is unsubstituted or substituted phenylalkyl, this is preferably unsubstituted or substituted benzyl and is in particular unsubstituted benzyl.

When $R_2$ is substituted phenyl, this is preferably phenyl substituted by 1 alkyl($C_1$–$C_{12}$).

When $R_3$ is alkyl, this is preferably ($C_3$–$C_{18}$) alkyl, e.g. ($C_8$–$C_{17}$)alkyl.

When $R_3$ is cycloalkyl, this is preferably cyclohexyl.

When $R_3$ is unsubstituted or substituted phenylalkyl, this is preferably unsubstituted or substituted phenylethyl. The substituents on the phenyl ring thereof are preferably 1 hydroxyl and/or 1 or 2 alkyl($C_1$–$C_4$) substituents.

When $R_3$ is substituted phenyl, this is preferably phenyl substituted by 1 chlorine, 1 m- or p-hydroxyl, 1 or 2 alkyl($C_1$–$C_4$), 1 alkoxy($C_1$–$C_4$) and/or 1 phenyl substituent.

When $R_3$ is a heterocycle, this is preferably bonded through the 2-position thereof, e.g. thiophen-2-yl.

When $R_3$ is a substituted heterocycle, this is preferably substituted by 1 chlorine or 1 alkyl($C_1$ or $C_2$).

When either of $R_4$ and $R_5$ are alkyl, this is preferably, independently, alkyl($C_1$–$C_4$), particularly methyl.

When either of $R_4$ and $R_5$ are substituted phenyl, this is preferably, independently, phenyl substituted by 1 alkyl($C_1$–$C_4$).

Preferably $R_1$ has one of the significances of $R_1'$, especially $R_1''$, and is in particular hydrogen.

Preferably $R_2$ has one of the significances of $R_2'$ and more preferably of $R_2''$, e.g. n-butyl.

Preferably $R_3$ has one of the significances of $R_3'$, and especially $R_3''$.

Preferably $R_4$ has one of the significances of $R_4'$ and is in particular phenyl.

Preferably $R_5$ has one of the significances of $R_5'$ and is more preferably alkyl, especially methyl.

Preferably the amine ligand(s) of the complexes(I) are of the formula $[NHR_1R_2]_p$.

Preferably the amine is a monodentate ligand, i.e. $p$ is preferably 2.

The complexes (I) are produced in accordance with a further aspect of the present invention by complexing the corresponding amine with the corresponding pyrazol-(5)-oxy nickel complex or, together with the corresponding pyrazolone-(5) compound, in free or alkali metal salt form, with a complexable nickel salt, preferably the latter.

The reaction is effected in known manner, in a solvent such as an alcohol, e.g. methanol, ethanol or n-propanol, preferably at an elevated temperature, conveniently at the boiling temperature of the reaction mixture under reflux. The complex usually precipitates out on cooling. Precipitation may be initiated or accelerated by the addition of water.

Examples of complexable nickel salts are the chloride, acetate, sulphate and tartrate salts.

The pyrazolone-(5) and amine compounds are either known or may be produced in manner known per se.

The complexes (I) are useful in the stabilization of sensitive material against the degradative effect of ultraviolet (U.V.) light.

Accordingly, the present invention provides a method of stabilizing sensitive material against the degradative effect of U.V. light which comprises "treating" said material with an effective amount of a complex (I).

By the term "treating" as employed herein is meant surface coating or incorporating the complex on or in, respectively, the material. The complex is preferably incorporated in the body of the material and more preferably is uniformly distributed therein.

Sensitive materials to which the method of the invention is suited include natural and synthetic polymeric materials such as natural polyalkylenes, e.g. natural rubber, natural polyethers such as natural cellulose, e.g. cotton, and natural polyamides, e.g. wool and silk, and synthetic polymeric materials such as synthetic polyalkylenes especially polyethylene and polypropylene, polyesters especially polyethylene terephthalates, cellulose acetobutyrate, polyvinylchloride, polymethyl methacrylates, polyphenylene oxides, polystyrene, polyurethanes, polycarbonates, polyacrylonitriles, polyamides, such as nylon, and polypropylene oxide and including synthetic co- and terpolymers such as copolymers of styrene and acrylonitrile or of styrene and butadiene and terpolymers of acrylonitrile, butadiene and styrene (ABS) and acrylic esters, styrene and acrylonitrile.

Preferably, the material treated comprises synthetic polymeric material, particularly polyethylene, polypropylene, polyester, polyamide, polyurethane, polyacrylonitrile, copolymers of styrene and acrylonitrile or styrene and butadiene, acrylonitrile-butadiene-styrene terpolymers and terpolymers of acrylic esters, styrene and acrylonitrile.

The stabilized materials may be in solid forms, e.g. panels, rods, coatings, sheets, films, tapes, fibres, granules or powders or in liquid or paste forms, e.g. solutions or emulsions.

The material to be stabilized may be treated in conventional manner.

In the treatment of kneadable solid materials, one important embodiment of the method of the invention comprises intimately mixing the complexes with a particulate, e.g. granular, form of material, e.g. polypropylene, in a kneader. The material may thereafter be formed into the required shape, e.g. by extrusion or injection moulding.

In the treatment of synthetic polymeric materials, a further important embodiment of the method of the invention comprises mixing the monomer or prepolymer with the complex prior to polymerization.

The amount of complex employed in the method of the invention will naturally vary depending, for example on the complex employed, the material to be treated and the mode of treatment. However, in general, satisfactory results may be obtained when the amount of complex employed is in the range 0.01 to 5%, preferably 0.05 to 1% of the weight of the material to be treated.

In the following Examples the parts and percentages are by weight. The temperatures are in degrees centigrade. The structures of the obtained compounds are verified by microanalysis and spectral analysis.

EXAMPLE 1

2.48 g of nickel acetate tetrahydrate are added at reflux temperature to 7.1 of 1-phenyl-3-methyl-4-lauroyl-pyrazolone-(5) and 7.4 g of dodecylamine in 50 ml of methanol. The mixture is kept at reflux temperature for 20 minutes. The precipitated blue-green complex is suctioned off at room temperature, washed with water and dried. The complex of formula

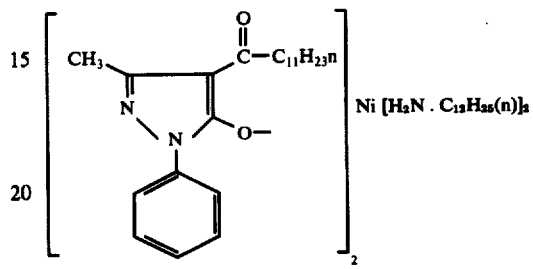

is obtained. M.P. 96°-98°.

EXAMPLE 2

The complex of the formula

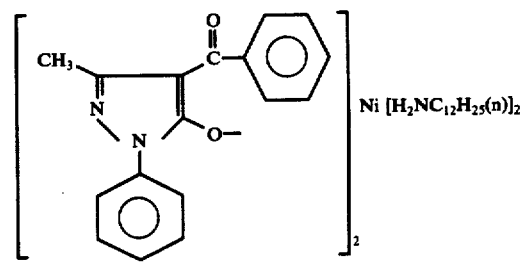

M.P. 91°-93° is produced in analogous manner to that described in Example 1. After refluxing, the methanol solvent is distilled off and the residue taken up in petroleum ether (B.P. 100°-120°), washed with water, dried and the ether distilled off.

The complexes set out below are produced in analogous manner to that described in Example 1.

TABLE 1

$$\left[ \begin{array}{c} R_5 \diagdown \quad \overset{O}{\underset{\parallel}{C}} - R_3 \\ N \diagdown \quad \diagup \\ \quad N \quad O- \\ \quad | \\ \quad R_4 \end{array} \right]_2 Ni[NH_2-R_2]_2$$

| Ex. No. | $R_3$ | $R_2$ | $R_4$ | $R_5$ | M.P. |
|---|---|---|---|---|---|
| 3 | —⟨O⟩— | —$C_4H_9$(n) | " | —$CH_3$ | 160–165° |
| 4 | " | —$C_8H_{17}$(n) | " | " | 118–121° |
| 5 | " | —$C_{18}H_{37}$(n) | " | " | resin |
| 6 | —$C_{11}H_{23}$(n) | | " | " | 91–94° |
| 7 | —⟨O⟩— | —$C_{12}H_{25}$(n) | —⟨H⟩ | " | 159–161° |

TABLE 1-continued
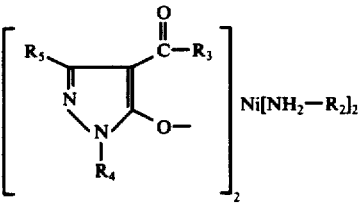
| Ex. No. | R₃ | R₂ | R₄ | R₅ | M.P. |
|---|---|---|---|---|---|
| 8 | " | —C₄H₉(n) | " | " | >200° |
| 9 | 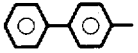 |  | " | " | >250° |
| 10 | " | —C₁₂H₂₅(n) | " | " | 145–147° |
| 11 | 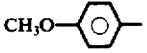 |  | " | " | 140–146° |
| 12 | 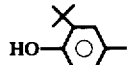 | " | " | " | 141–147° |
| 13 | 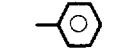 | " | " | " | 190–193° |
| 14 |  | " | " | " | >200° |
| 15 | 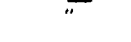 | —C₁₂H₂₅(n) | " | " | 94–97° |
| 16 | " |  | " | " | 230–231° |
| 17 | " |  | " | " | 198–203° |
| 18 | 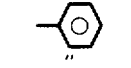 |  | " | " | 237–239° |
| 19 | " | 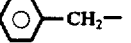 | " | " | 125–129° |
| 20 | " | 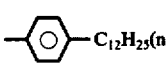 | " | " | resin |
| 21 | —C₁₅H₃₁(n) |  | " | " | 98–102° |
| 22 | —C₁₇H₃₅(n) | " | " | " | 92–95° |
| 23 |  | 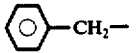 | " | " | >200° |
| 24 | " | 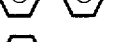 | " | " | >200° |
| 25 | " |  | " | " | resin |
| 26 |  | 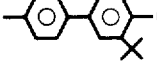 | " | —CH₃ | 98–107° |
| 27 | —C₉H₁₉(n) |  | " | " | 106–107° |
| 28 |  |  | " |  | 110–120° |
| 29 | —C₉H₁₉(n) | " | " | —CH₃ | 97–100° |
| 30 | 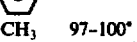 | —C₄H₉(n) | " | " | 245–250° |
| 31 | 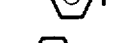 | " | " | 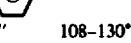 | 108–130° |
| 32 | —C₈H₁₇(n) | " | " | " | 113–114° |
| 33 | " | 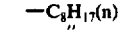 | " | " | 124–126° |

TABLE 1-continued $$\left[\begin{array}{c} R_5 \\ \diagdown \\ N \\ | \\ R_4 \end{array} \begin{array}{c} O \\ \| \\ C-R_3 \\ \diagup \\ O- \end{array}\right]_2 Ni[NH_2-R_2]_2$$

| Ex. No. | $R_3$ | $R_2$ | $R_4$ | $R_5$ | M.P. |
|---|---|---|---|---|---|
| 34 | –⌬– | –C₄H₉(n) | CH₃–⌬– | –CH₃ | 175–180° |
| 35 | –⌬– | –C₄H₉(n) | –⌬– | nC₃H₇– | 237–242° |
| 36 | " | –⌬–⁺ | " | " | 248–250° |
| 37 | " | H–⌬– | " | " | 235–237° |
| 38 | –C₉H₁₉(n) | –⌬–CH₂– | " | nC₃H₇– | 99–102° |
| 39 | " | –C₈H₁₇(n) | " | " | 94–105° |
| 40 | (thienyl) | –CH₂–⌬– | " | CH₃ | 90–105° |

+ = –C(CH₃)₃

EXAMPLE 41

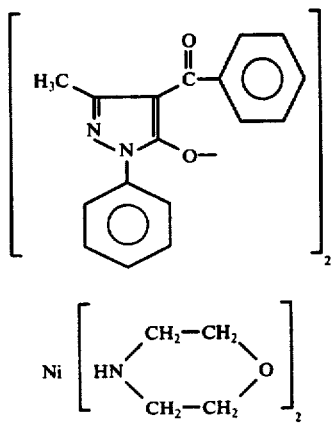

M.P. > 200° C

EXAMPLE 42

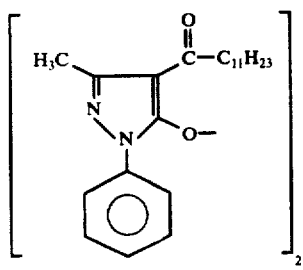

-continued

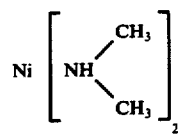

M.P. 134°–137° C

TABLE 2

$$\left[\begin{array}{c} R_5 \\ \diagdown \\ N \\ | \\ \text{Ph} \end{array} \begin{array}{c} O \\ \| \\ C-R_3 \\ \diagup \\ O- \end{array}\right]_2 Ni[NH_2-CH_2-CH_2-OH]$$

| Ex. No. | $R_3$ | $R_5$ | M.P. |
|---|---|---|---|
| 43 | –C₉H₁₉(n) | –CH₃ | >200° |
| 44 | –C₁₁H₂₃(n) | –CH₃ | >200° |
| 45 | –⌬– | –CH₃ | >200° |
| 46 | –⌬–⁺ | –CH₃ | >200° |
| 47 | –⌬–⁺ | –C₃H₇(n) | >200° |

TABLE 2-continued

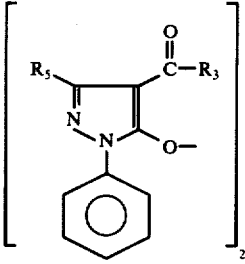

| Ex. No. | $R_3$ | $R_5$ | M.P. |
|---|---|---|---|
| 48 | —C₆H₄—C₆H₅ (biphenyl) | —C₆H₅ (phenyl) | >200° |

EXAMPLE 49

52.2 g 1-phenyl-3-methyl-pyrazolone-(5) and 19.8 g of CuO are added to 180 g of dioxane. With stirring and over the course of 1 hour at 90°, 59.0 g of para-tert.butyl-benzoyl chloride are added to the mixture. After completion of the reaction, the dioxane is distilled off and the residue taken up in 100 g of toluene, 35 g of concentrated HCl and 90 g of water and stirred for 30 minutes at 90° until the organic phase separates. The organic phase is separated, washed with water until neutral and finally the toluene distilled off. The dark brown residue is then reacted with 35.6 g nickel chloride hexahydrate in 300 g of methanol to produce a green solution. The green solution is reacted with 60 g of cyclohexylamine with cooling over 10 minutes in an ice bath, the reaction product precipitating out. The product is washed with methanol and then water and dried at 90° C. The following compound

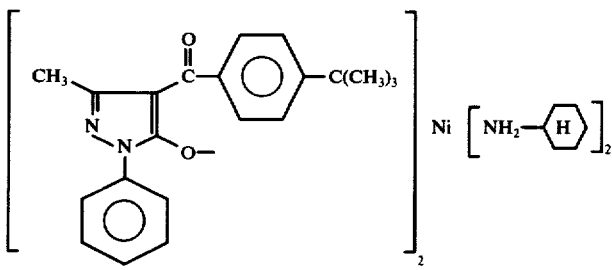

is obtained. M.P. 242°-250°.

METHOD EXAMPLE

3 Samples of unstabilized polypropylene and 0.5% by weight of the complex of Example 1, 2 and 14 are intimately kneaded on a roll mill at 180°. Each sample is extruded into sheets of 0.3 mm thickness. Specimens of the sheets were tested for stability in the Klimatest apparatus by the De La Rue method at 40° and 75% relative atmospheric humidity, with thorough ventilation and irradiation by 16 sun lamps and 16 black lamps of Philips manufacture. The degree of stabilization is determined by comparing the effect of the polypropylene sample with the effect obtained with polypropylene containing no complex. The result in each case showed a stabilizing effect by the complex.

Specimens of an unstabilized polyvinyl chloride sheet and a sheet containing 0.5% of the complex of Example 10 in Table 1 were tested in analogous manner in the Klimatest apparatus with a similar result.

Analogous results are obtained for polyethylene, acrylonitrile-butadiene-styrene terpolymer, polyethylene terephthalate, cellulose acetobutyrate, polyamine 6, polystyrene, polycarbonate and polyurethane.

Having thus disclosed the invention, what we claim is:

1. A stabilized composition comprising a natural or synthetic polymeric material susceptible to degradation under the effect of ultraviolet light and incorporated therein, in a sufficient amount to prevent said degradation, a nickel complex of the formula:

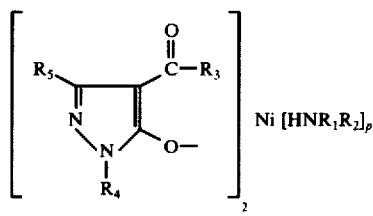

wherein either $R_1$ is hydrogen, alkyl ($C_1$–$C_8$) or —CH$_2$CH$_2$OH
and $R_2$ is alkyl ($C_1$–$C_{18}$); alkyl ($C_1$–$C_{18}$) monosubstituted by hydroxy, alkoxy ($C_1$–$C_4$), piperidino or morpholino; cyclohexyl; phenylalkyl ($C_7$ or $C_8$); phenylalkyl ($C_7$ or $C_8$) substituted on the phenyl nucleus by a total of 1 to 3 substituents, each substituent selected from the group consisting of alkyl ($C_1$–$C_4$) and hydroxy, with the proviso that there is a maximum of 2 alkyl substituents and a maximum of 1 hydroxy substituent; phenyl; phenyl monosubstituted by alkyl ($C_1$–$C_{12}$); phenyl monosubstituted by chloro; phenyl monosubstituted by unsubstituted phenyl or phenyl substituted by a total of 1 to 3 substituents, each substituent selected from the group consisting of alkyl ($C_1$–$C_4$) and hydroxy, with the proviso that there is a maximum of 1 hydroxy substituent and a maximum of 2 alkyl substituents;

or $R_1$ and $R_2$, together with the —NH— group to which they are bound, form a piperidine, morpholine, pyrrolidine or imidazolidine ring;

$R_3$ is alkyl ($C_1$–$C_{22}$); alkyl ($C_1$–$C_{21}$)-thio-alkyl ($C_1$–$C_{21}$) with $C_2$–$C_{22}$ in the aggregate thereof; alkyl ($C_1$–$C_4$) monosubstituted by chloro; alkyl ($C_1$–$C_4$) disubstituted by chloro; cycloalkyl ($C_5$–$C_{12}$); cycloalkyl ($C_5$–$C_{11}$) alkyl ($C_1$–$C_7$) with $C_6$–$C_{12}$ in the aggregate thereof; phenylalkyl ($C_7$–$C_{12}$); phenylalkyl ($C_7$–$C_{12}$) monosubstituted on the phenyl nucleus by hydroxy; phenylalkyl ($C_7$–$C_{12}$) disubstituted on the phenyl nucleus by hydroxy; phenylalkyl ($C_7$–$C_{12}$) monosubstituted on the phenyl nucleus by alkyl ($C_1$–$C_{12}$);

phenylalkyl (C$_7$–C$_{12}$) disubstituted on the phenyl nucleus by alkyl (C$_1$–C$_{12}$); phenylalkyl (C$_7$–C$_{12}$) monosubstituted on the phenyl nucleus by cycloalkyl (C$_5$–C$_{12}$); phenylalkyl (C$_7$–C$_{12}$) monosubstituted on the phenyl nucleus by cycloalkyl (C$_5$–C$_{11}$)-alkyl (C$_1$–C$_7$) with C$_6$–C$_{12}$ in the aggregate thereof; phenylalkyl (C$_7$–C$_{12}$) monosubstituted on the phenyl nucleus by hydroxy and monosubstituted on the phenyl nucleus by alkyl (C$_1$–C$_{12}$); phenylalkyl (C$_7$–C$_{12}$) monosubstituted on the phenyl nucleus by hydroxy and disubstituted on the phenyl nucleus by alkyl (C$_1$–C$_{12}$); phenylalkyl (C$_7$–C$_{12}$) monosubstituted on the phenyl nucleus by hydroxy and monosubstituted on the phenyl nucleus by cycloalkyl (C$_5$–C$_{12}$); phenylalkyl (C$_7$–C$_{12}$) monosubstituted on the phenyl nucleus by hydroxy and monosubstituted on the phenyl nucleus by cycloalkyl C$_5$–C$_{11}$)-alkyl (C$_1$–C$_7$) with C$_6$–C$_{12}$ in the aggregate thereof; phenylalkyl (C$_7$–C$_{12}$) disubstituted on the phenyl nucleus by hydroxy and monosubstituted on the phenyl nucleus by alkyl (C$_1$–C$_{12}$); phenylalkyl (C$_7$–C$_{12}$) disubstituted on the phenyl nucleus by hydroxy and disubstituted on the phenyl nucleus by alkyl (C$_1$–C$_{12}$); phenylalkyl (C$_7$–C$_{12}$) disubstituted on the phenyl nucleus by hydroxy and monosubstituted on the phenyl nucleus by cycloalkyl (C$_5$–C$_{12}$); phenylalkyl (C$_7$–C$_{12}$) disubstituted on the phenyl nucleus by hydroxy and monosubstituted on the phenyl nucleus by cycloalkyl (C$_5$–C$_{11}$)-alkyl (C$_1$–C$_7$) with C$_6$–C$_{12}$ in the aggregate thereof; phenyl; phenyl substituted by a total of 1 to 3 substituents, said substituents having not more than 18 carbon atoms, each substituent being selected from the group consisting of halo, cyano, meta-hydroxy, para-hydroxy, alkyl (C$_1$–C$_{12}$), alkoxy (C$_1$–C$_{12}$), phenyl, R$_6$–O and R$_6$–SO$_2$, wherein R$_6$ is phenyl, phenyl monosubstituted by alkyl (C$_1$–C$_8$) or phenyl disubstituted by alkyl (C$_1$–C$_8$), with the proviso that there is a maximum of 2 halo substituents, a maximum of 1 cyano substituent, only one of substituents meta-hydroxy and para-hydroxy, a maximum of 2 alkyl (C$_1$–C$_{12}$) substituents, a maximum of 2 alkoxy (C$_1$–C$_{12}$) substituents and only one of substituents R$_6$—O— and R$_6$—SO$_2$—; a heterocyclic ring selected from furyl, thienyl, benzothienyl, indolyl, pyridyl and quinoxalinyl; or a furyl, thienyl, benzothienyl, indolyl, pyridyl or quinoxalinyl ring substituted by a total of one or two substituents, each substituent being selected from the group consisting of halo, alkyl (C$_1$–C$_4$) and alkoxy (C$_1$–C$_4$);

R$_4$ and R$_5$ are each, independently, alkyl (C$_1$–C$_8$); phenyl; or phenyl substituted by a total of 1 to 3 substituents, each substituent being selected froom the group consisting of halo and alkyl (C$_1$–C$_4$), with the proviso that there is a maximum of 1 halo substituent and a maximum of 2 alkyl (C$_1$–C$_4$) substituents; and p is 1 when the amine ligand is bidentate, and
p is 2 when the amine ligand is monodentate.

2. A method of stabilizing a natural or synthetic polymeric material susceptible to degradation under the effect of ultraviolet light which comprises treating said material with a stabilizing effective amount of a nickel complex of the formula:

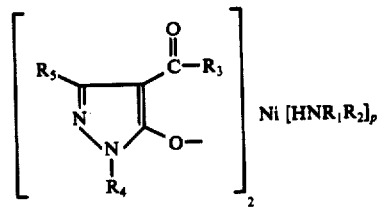

wherein either R$_1$ is hydrogen, alkyl (C$_1$–C$_8$) or —CH$_2$CH$_2$OH and R$_2$ is alkyl (C$_1$–C$_{18}$); alkyl (C$_1$–C$_{18}$) monosubstituted by hydroxy, alkoxy (C$_1$–C$_4$), piperidino or morpholino; cyclohexyl; phenylalkyl (C$_7$ or C$_8$); phenylalkyl (C$_7$ or C$_8$) substituted oon the phenyl nucleus by a total of 1 to 3 substituents, each substituent selected from the group consisting of alkyl (C$_1$–C$_4$) and hydroxy, with the proviso that there is a maximum of 2 alkyl substituents and a maximum of 1 hydroxy substituent; phenyl; phenyl monosubstituted by alkyl (C$_1$–C$_{12}$); phenyl monosubstituted by chloro; phenyl monosubstituted by unsubstituted phenyl or phenyl substituted by a total of 1 to 3 substituents, each substituent selected from the group consisting of alkyl (C$_1$–C$_4$) and hydroxy, with the proviso that there is a maximum of 1 hydroxy substituent and a maximum of 2 alkyl substituents;

or R$_1$ and R$_2$, together with the —NH— group to which they are bound, form a piperidine, morpholine, pyrrolidine or imidazolidine ring;

R$_3$ is alkyl (C$_1$–C$_{22}$); alkyl (C$_1$–C$_{21}$)-thioalkyl (C$_1$–C$_{21}$) with C$_2$–C$_{22}$ in the aggregate thereof; alkyl (C$_1$–C$_4$) monosubstituted by chloro; alkyl (C$_1$–C$_4$) disubstituted by chloro; cycloalkyl (C$_5$–C$_{12}$); cycloalkyl (C$_5$–C$_{11}$) alkyl (C$_1$–C$_7$) with C$_6$–C$_{12}$ in the aggregate thereof; phenylalkyl (C$_7$–C$_{12}$); phenylalkyl (C$_7$–C$_{12}$) monosubstituted on the phenyl nucleus by hydroxy; phenylalkyl (C$_7$–C$_{12}$) disubstituted on the phenyl nucleus by hydroxy; phenylalkyl (C$_7$–C$_{12}$) monosubstituted on the phenyl nucleus by alkyl (C$_1$–C$_{12}$); phenylalkyl (C$_7$–C$_{12}$) disubstituted on the phenyl nucleus by alkyl (C$_1$–C$_{12}$); phenylalkyl (C$_7$–C$_{12}$) monosubstituted on the phenyl nucleus by cycloalkyl (C$_5$–C$_{12}$); phenylalkyl (C$_7$–C$_{12}$) monosubstituted on the phenyl nucleus by cycloalkyl (C$_5$–C$_{11}$) alkyl (C$_1$–C$_7$) with C$_6$–C$_{12}$ in the aggregate thereof; phenylalkyl (C$_7$–C$_{12}$) monosubstituted on the phenyl nucleus by hydroxy and monosubstituted on the phenyl nucleus by alkyl (C$_1$–C$_{12}$); phenylalkyl (C$_7$–C$_{12}$) monosubstituted on the phenyl nucleus by hydroxy and disubstituted on the phenyl nucleus by alkyl (C$_1$–C$_{12}$); phenylalkyl (C$_7$–C$_{12}$) monosubstituted on the phenyl nucleus by hydroxy and monosubstituted on the phenyl nucleus by cycloalkyl (C$_5$–C$_{12}$); phenylalkyl (C$_7$–C$_{12}$) monosubstituted on the phenyl nucleus by hydroxy and monosubstituted on the phenyl nucleus by cycloalkyl (C$_5$–C$_{11}$)-alkyl (C$_1$–C$_7$) with C$_6$–C$_{12}$ in the aggregate thereof; phenylalkyl (C$_7$–C$_{12}$) disubstituted on the phenyl nucleus by hydroxy and monosubstituted on the phenyl nucleus by alkyl (C$_1$–C$_{12}$); phenylalkyl (C$_7$–C$_{12}$) disubstituted on the phenyl nucleus by hydroxy and disubstituted on the phenyl nucleus by alkyl (C$_1$–C$_{12}$); phenylalkyl (C$_7$–C$_{12}$) disubstituted on the phenyl nucleus by hydroxy and monosubstituted on the phenyl nucleus by cycloalkyl (C₅–C₁₂); phenylalkyl (C₇–C₁₂) disubstituted on the phenyl nucleus by hydroxy and monosubstituted on the phenyl nucleus by cycloalkyl (C₅–C₁₁)-alkyl (C₁–C₇) with C₆–C₁₂ in the aggregate thereof; phenyl; phenyl substituted by a total of 1 to 3 substituents, said substituents having not more than 18 carbon atoms, each substituent being selected from the group consisting of halo, cyano, meta-hydroxy, para-hydroxy, alkyl (C₁–C₁₂), alkoxy (C₁–C₁₂), phenyl, R₆–O and R₆–SO₂, wherein R₆ is phenyl, phenyl monosubstituted by alkyl (C₁–C₈) or phenyl disubstituted by alkyl (C₁–C₈), with the proviso that there is a maximum of 2 halo substituents, a maximum of 1 cyano substituent, only one of substituents meta-hydroxy and para-hydroxy, a maximum of 2 alkyl (C₁–C₁₂) subistituents, a maximum of 2 alkoxy (C₁–C₁₂) substituents and only one of substituents R₆—O— and R₆—SO₂—; a heterocyclic ring selected from furyl, thienyl, benzothienyl, indolyl, pyridyl and quinoxalinyl; or a furyl thienyl, benzothienyl, indolyl, pyridyl or quinoxalinyl ring substituted by a total of one or two substituents, each substituent being selected from the group consisting of halo, alkyl (C₁–C₄) and alkoxy (C₁–C);

R₄ and R₅ are each, independently, alkyl (C₁–C₈); phenyl; or phenyl substituted by a total of 1 to 3 substituents, each substituent being selected from the group consisting of halo and alkyl (C₁–C₄), with the proviso that there is a maximum of 1 halo substituent and a maximum of 2 alkyl (C₁–C₄) substituents; and

*p* is 1 when the amine ligand is bidentate, and is 2 when the amine ligand is monodentate.

3. A method according to claim 2, wherein the material is a synthetic polymer.

4. A method according to claim 3, wherein the synthetic polymer is selected from polyethylene, polypropylenes polyester, polyamide, polyurethane, polyacrylonitrile, copolymers of styrene and acrylonitrile or styrene and butadiene, acrylonitrile-butadiene-styrene terpolymers and terpolymers of acrylic esters, styrene and acrylonitrile.

5. A method according to claim 2, wherein said material is treated with a compound of the formula:

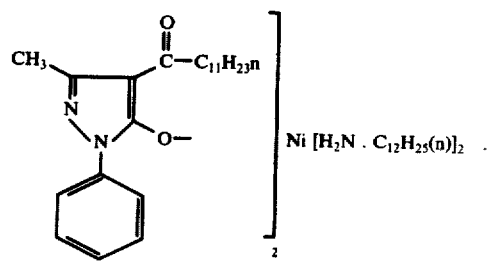

6. A method according to claim 2, wherein said material is treated with a compound of the formula:

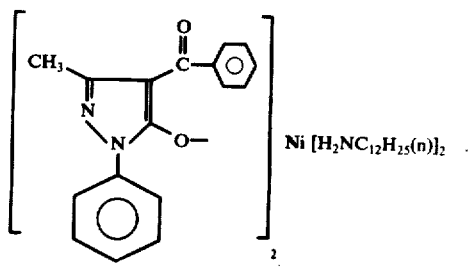

7. A method according to claim 2, wherein said material is treated with a compound of the formula:

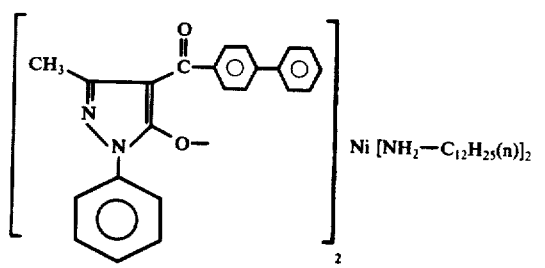

8. A method according to claim 2, wherein said material is treated with a compound of the formula:

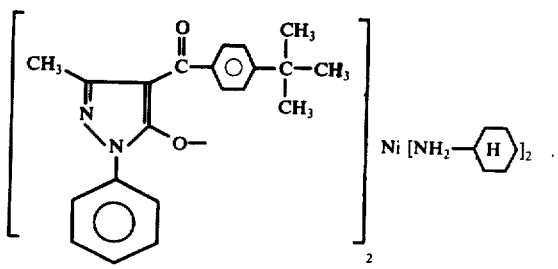

* * * * *